(12) United States Patent
Li

(10) Patent No.: US 10,706,333 B2
(45) Date of Patent: Jul. 7, 2020

(54) MEDICAL IMAGE ANALYSIS METHOD, MEDICAL IMAGE ANALYSIS SYSTEM AND STORAGE MEDIUM

(71) Applicant: BOE TECHNOLOGY GROUP CO., LTD., Beijing (CN)

(72) Inventor: Yingying Li, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 123 days.

(21) Appl. No.: 15/954,981

(22) Filed: Apr. 17, 2018

(65) Prior Publication Data

US 2019/0065897 A1    Feb. 28, 2019

(30) Foreign Application Priority Data

Aug. 28, 2017  (CN) .......................... 2017 1 0751978

(51) Int. Cl.
| | |
|---|---|
| *G06K 9/00* | (2006.01) |
| *G06K 9/62* | (2006.01) |
| *G16H 30/40* | (2018.01) |
| *G06N 3/08* | (2006.01) |
| *G06K 9/46* | (2006.01) |
| *G16H 50/20* | (2018.01) |
| *G06N 20/10* | (2019.01) |
| *G06N 3/04* | (2006.01) |

(52) U.S. Cl.
CPC .............. *G06K 9/628* (2013.01); *G06K 9/46* (2013.01); *G06K 9/6257* (2013.01); *G06K 9/6269* (2013.01); *G06K 9/6277* (2013.01); *G06N 3/0454* (2013.01); *G06N 3/08* (2013.01); *G06N 3/084* (2013.01); *G06N 20/10* (2019.01); *G16H 30/40* (2018.01); *G16H 50/20* (2018.01); *G06K 2209/05* (2013.01); *G06N 3/0445* (2013.01)

(58) Field of Classification Search
None
See application file for complete search history.

(56) References Cited

U.S. PATENT DOCUMENTS

| | | | |
|---|---|---|---|
| 9,739,783 B1 * | 8/2017 | Kumar ............. | G01N 33/57492 |
| 2013/0208964 A1 | 8/2013 | Dwivedi | |
| 2016/0117818 A1 * | 4/2016 | Park ..................... | G06T 7/0012 |
| | | | 382/131 |
| 2016/0148376 A1 * | 5/2016 | Ryu ...................... | G06T 7/0012 |
| | | | 382/131 |

(Continued)

FOREIGN PATENT DOCUMENTS

| | | |
|---|---|---|
| CN | 103180878 A | 6/2013 |
| CN | 106056595 A | 10/2016 |

(Continued)

OTHER PUBLICATIONS

First Chinese Office Action dated Aug. 13, 2019.

*Primary Examiner* — Delomia L Gilliard
(74) *Attorney, Agent, or Firm* — Dilworth & Barrese, LLP.; Michael J. Musella, Esq.

(57) ABSTRACT

A medical image analysis method, a medical image analysis system and a storage medium. The medical image analysis method includes: obtaining a medical image; processing the medical image by using a neural network, so as to determine a classification result of the medical image; and inputting the medical image into a computer aided diagnosis device corresponding to the classification result.

20 Claims, 5 Drawing Sheets

(56) References Cited

U.S. PATENT DOCUMENTS

| | | | |
|---|---|---|---|
| 2018/0144214 A1* | 5/2018 | Hsieh | G06T 7/0012 |
| 2018/0144465 A1* | 5/2018 | Hsieh | G06T 7/0012 |
| 2018/0144466 A1* | 5/2018 | Hsieh | G06F 19/00 |
| 2019/0172581 A1* | 6/2019 | Zlotnick | G06N 20/00 |
| 2019/0237186 A1* | 8/2019 | El-Baz | A61B 5/201 |

FOREIGN PATENT DOCUMENTS

| | | | |
|---|---|---|---|
| CN | 106156793 A | 11/2016 | |
| CN | 106777953 A | 5/2017 | |
| CN | 106780482 A | 5/2017 | |

* cited by examiner

MEDICAL IMAGE ANALYSIS METHOD, MEDICAL IMAGE ANALYSIS SYSTEM AND STORAGE MEDIUM

The present application claims priority to Chinese patent application No. 201710751978.5, filed Aug. 28, 2017, the entire disclosure of which is incorporated herein by reference as part of the present application.

TECHNICAL FIELD

Embodiments of the present disclosure relate to a medical image analysis method, a medical image analysis system and a storage medium.

BACKGROUND

Deep learning is a type of machine learning and can perform characterization learning on data. Deep learning can obtain features by using unsupervised or semi-supervised feature learning and a stratified feature extraction algorithm. A basic structure of deep learning is a deep learning neural network. The deep learning neural network is an artificial neural network with at least one hidden layer, and can form abstract high-level features representing attribute categories by combining lower-level features, so as to find distributed representations of data.

SUMMARY

At least one embodiment of the present disclosure provides a medical image analysis method, which comprises: obtaining a medical image; processing the medical image by using a neural network, so as to determine a classification result of the medical image; and inputting the medical image into a computer aided diagnosis device corresponding to the classification result.

For example, in the medical image analysis method provided by at least one embodiment of the present disclosure, the processing the medical image by using the neural network, so as to determine the classification result of the medical image comprises: extracting features of the medical image by the neural network; and classifying the medical image by a classifier based on the features of the medical image to obtain the classification result.

For example, in the medical image analysis method provided by at least one embodiment of the present disclosure, the classifying the medical image by the classifier based on the features of the medical image to obtain the classification result comprises: based on the features of the medical image, calculating a plurality of scores that the medical image belongs to a plurality of different categories by the classifier; and determining the classification result of the medical image according to sorting of the plurality of scores.

For example, in the medical image analysis method provided by at least one embodiment of the present disclosure, the plurality of scores is a plurality of prediction probabilities, and the classification result corresponds to a maximum prediction probability from the plurality of prediction probabilities.

For example, in the medical image analysis method provided by at least one embodiment of the present disclosure, the computer aided diagnosis device is configured to analyze the features of the medical image corresponding to the classification result, the computer aided diagnosis device is a part of a computer aided diagnosis device group, and respective computer aided diagnosis devices in the computer aided diagnosis device group are configured to analyze features of medical images of different categories.

For example, in the medical image analysis method provided by at least one embodiment of the present disclosure, a quantity of computer aided diagnosis devices in the computer aided diagnosis device group is identical to a quantity of the plurality of scores.

For example, in the medical image analysis method provided by at least one embodiment of the present disclosure, before obtaining the medical image, the medical image analysis method further comprises: in a training phase, training the neural network with sample images in a medical image database to generate a parameter of the neural network.

For example, in the medical image analysis method provided by at least one embodiment of the present disclosure, a loss function in the training phase comprises a log-likelihood loss function, and the log-likelihood loss function is expressed as:

$$C = -\ln a_y$$

where C denotes the log-likelihood loss function, y denotes a category of the medical image, and $a_y$ denotes a prediction probability corresponding to y.

At least one embodiment of the present disclosure further provides a medical image analysis system, which is connected with a computer aided diagnosis device. The medical image analysis system comprises a neural network and an image acquisition device, the neural network comprises an input layer and an output layer, the image acquisition device is connected with the input layer of the neural network, and the computer aided diagnosis device is connected with the output layer of the neural network. The image acquisition device is configured to obtain a medical image. The neural network is configured to receive and process the medical image, so as to determine a classification result of the medical image, and input the medical image into the computer aided diagnosis device according to the classification result. The computer aided diagnosis device is configured to analyze the medical image.

For example, in the medical image analysis system provided by at least one embodiment of the present disclosure, the neural network comprises a classifier, the neural network is configured to extract features of the medical image, and the classifier is configured to classify the medical image based on the features of the medical image to obtain the classification result.

For example, in the medical image analysis system provided by at least one embodiment of the present disclosure, the classifier comprises at least one of a support vector machine (SVM) classifier and a SoftMax classifier.

For example, in the medical image analysis system provided by at least one embodiment of the present disclosure, the classifier is configured to: based on the features of the medical image, calculate a plurality of scores that the medical image belongs to a plurality of different categories; and determine the classification result of the medical image according to sorting of the plurality of scores.

For example, in the medical image analysis system provided by at least one embodiment of the present disclosure, the plurality of scores is a plurality of prediction probabilities, and the classification result corresponds to a maximum prediction probability from the plurality of prediction probabilities.

For example, in the medical image analysis system provided by at least one embodiment of the present disclosure, the computer aided diagnosis device is configured to analyze the features of the medical image corresponding to the classification result, the computer aided diagnosis device is a part of an computer aided diagnosis device group, and respective computer aided diagnosis devices of the computer aided diagnosis device group are configured to analyze features of medical images of different categories.

For example, in the medical image analysis system provided by at least one embodiment of the present disclosure, a quantity of computer aided diagnosis devices in the computer aided diagnosis device group is identical to a quantity of the plurality of scores.

For example, in the medical image analysis system provided by at least one embodiment of the present disclosure, the neural network is a convolutional neural network.

At least one embodiment of the present disclosure further provides a medical image analysis system, which is connected with a computer aided diagnosis device. The medical image analysis system comprises: a storage, configured to store non-transitory computer-readable instructions; and a processor, configured to execute the non-transitory computer-readable instructions. The non-transitory computer-readable instructions, as executed by the processor, cause the processor to perform steps including: obtaining a medical image; processing the medical image by using a neural network, so as to determine a classification result of the medical image; and inputting the medical image into a computer aided diagnosis device corresponding to the classification result.

For example, in the medical image analysis system provided by at least one embodiment of the present disclosure, processing the medical image by using the neural network, so as to determine the classification result of the medical image comprises: extracting features of the medical image by the neural network; and classifying the medical image by a classifier based on the features of the medical image to obtain the classification result.

For example, in the medical image analysis system provided by at least one embodiment of the present disclosure, classifying the medical image by the classifier based on the features of the medical image to obtain the classification result comprises: based on the features of the medical image, calculating a plurality of scores that the medical image belongs to a plurality of different categories by the classifier; and determining the classification result of the medical image according to sorting of the plurality of scores.

At least one embodiment of the present disclosure further provides a storage medium, configured to store non-transitory computer-readable instructions, the non-transitory computer-readable instructions, as executed by a computer, cause the computer to perform steps including: obtaining a medical image; processing the medical image by using a neural network, so as to determine a classification result of the medical image; and inputting the medical image into a computer aided diagnosis device corresponding to the classification result.

BRIEF DESCRIPTION OF THE DRAWINGS

In order to clearly illustrate the technical solutions of the embodiments of the disclosure, the drawings of the embodiments will be briefly described in the following; it is obvious that the described drawings are only related to some embodiments of the disclosure and thus are not limitative to the disclosure.

DETAILED DESCRIPTION

Figure 1:
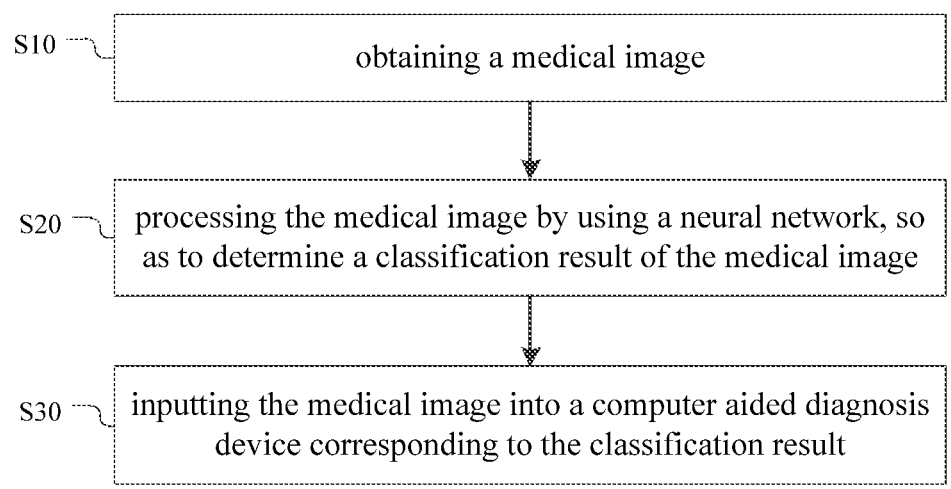
FIG. 1 is a schematic flow chart of a medical image analysis method provided by an embodiment of the present disclosure.

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Unless otherwise defined, all the technical and scientific terms used herein have the same meanings as commonly understood by one of ordinary skill in the art to which the present disclosure belongs. The terms "first," "second," etc., which are used in the present disclosure, are not intended to indicate any sequence, amount or importance, but distinguish various components. The terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly.

In order to make the following description of the embodiments of the present disclosure clear and concise, the present disclosure omits detailed description of known functions and known components.

A deep learning neural network can be applied to pictures, videos, speech recognition, and other aspects. The deep learning neural network can improve the accuracy of recognition, reduce the time of extracting features and improve computational efficiency. Due to the deepening of an artificial neural network structure, the improvement of the algorithm, the increase of the computational ability brought by a graphics processing unit (GPU), the increase of training data and other factors, the deep learning neural network is gradually applied to text processing, natural language understanding, face recognition, medical diagnosis, human-computer dialogue and emotional computing and other aspects.

In the following description, a computer aided diagnosis device, also referred to as CAD, is a computer system that assists in interpreting medical images. The computer aided diagnosis device can provide parameters or state descriptions regarding contents of a medical image according to the contents of the medical image, and a doctor or the like can diagnose disease of a patient based on these parameters or state descriptions, in combination with data obtained from clinical examination, biopsy and the like, and in combination with personal diagnosis experience.

Embodiments of the present disclosure provide a medical image analysis method, a medical image analysis system, and a storage medium, which can integrate various types of medical-image computer aided diagnosis devices, so as to achieve automatically analyzing many types of medical images, improve operating efficiency of the computer aided diagnosis device (CAD), and alleviate scarcity and unevenness of medical resources.

Several embodiments of the present disclosure are described in details below, but the present disclosure is not limited to these specific embodiments.

Figure 2:
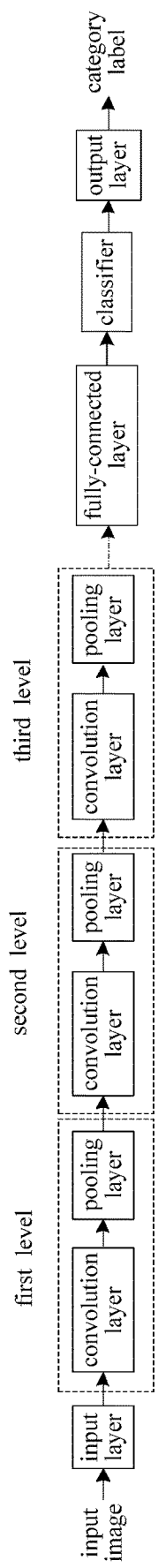
FIG. 2 is an exemplary structure of a convolutional neural network.

FIG. 1 is a schematic flow chart of a medical image analysis method provided by an embodiment of the present disclosure; FIG. 2 is an exemplary structure of a convolutional neural network.

For example, as shown in FIG. 1, a medical image analysis method provided by an embodiment of the present disclosure may comprise, but not limited to, the following steps:

Step S10: obtaining a medical image;

Step S20: processing the medical image by using a neural network, so as to determine a classification result of the medical image; and Step S30: inputting the medical image into a computer aided diagnosis device corresponding to the classification result.

The medical image analysis method provided by the embodiments of the present disclosure can integrate various types of medical-image computer aided diagnosis devices, so as to achieve automatically analyzing many types of medical images, improve operating efficiency of the computer aided diagnosis device (CAD), and alleviate scarcity and unevenness of medical resources.

For example, in the step S10, the medical image may be obtained by an image acquisition device. In the present disclosure, the image acquisition device, for example, may comprise an ultrasound device, an X-ray device, a magnetic resonance imaging device, a nuclear medicine device, a medical optical device, a thermal imaging device and so on, and the present disclosure is not limited thereto.

For example, the medical image may be various types of images. For example, according to a device for obtaining the medical image, the medical image may comprise an ultrasound image, a X-ray computed tomography (CT) image, a magnetic resonance imaging (MRI) image, a digital subtraction angiography (DSA) image, a positron emission computed tomography (PET) image and so on. According to the content of the medical image, the medical image may comprise a brain tissue MRI image, a spinal cord MRI image, a fundus image, a blood vessel image, a pancreas CT image, a lung CT image and so on.

For example, the medical image may be a two-dimensional image, or a three-dimensional image. The medical image may be a grayscale image or a color image.

It should be noted that, before using the neural network to process the medical image, the medical image analysis method may further comprise a step of preprocessing the medical image. A preprocessing operation can eliminate irrelevant information or noise information from the medical image, so as to better identify and classify the medical image. The preprocessing operation, for example, may comprise performing image scaling, gamma correction, image enhancement, noise reduction or filtering, etc. on the medical image. For example, the filtering operation on the medical image mainly comprises a spatial domain method and a frequency domain method. The spatial domain method mainly comprises smoothing and filtering operations, and the frequency domain method mainly comprises Fourier transform and other frequency domain transform operations.

For example, in the step S20, the processing the medical image by using the neural network, so as to determine the classification result of the medical image may comprise the following steps:

Step S201: extracting features of the medical image by the neural network; and

Step S202: classifying the medical image by a classifier based on the features of the medical image to obtain the classification result.

For example, the neural network may comprise a convolutional neural network (CNN), a stacked auto encoder network, a sparse auto encoder network, a recurrent neural network (RNN), a deep belief network and the like. The embodiments of the present disclosure may process the medical image by adopting one or a combination of several of the above neural networks.

For example, in an embodiment, the neural network is a convolutional neural network. The convolutional neural network can be used to extract feature information of the medical image, so as to accurately determine a type of the medical image and improve the classification accuracy of the medical image. The convolutional neural network, for example, is a deep convolutional neural network (Deep CNN).

For example, as shown in FIG. 2, an input image is input into the convolutional neural network through an input layer, and then the input image is successively processed by several processing processes (such as each level in FIG. 2) to output a category label, and these levels constitute hidden layers of the neural network. Main components of the convolutional neural network comprise: a plurality of convolution layers, a plurality of pooling layers (also known as sub-sampling layers) and a fully-connected layer. A complete convolutional neural network is composed of these three layers. For example, FIG. 2 only shows three levels of the convolutional neural network, namely a first level, a second level and a third level, and each level comprises a convolution layer and a pooling layer. Thus, a processing process of each level may comprise: performing convolution and sub-sampling on the input image. According to actual needs, the processing process of each level may also comprise local constant normalization (LCN) and so on.

The convolution layer is a core layer of the convolutional neural network. The convolution layer can apply several filters (namely convolution kernels) to the input image to extract many types of features. Each filter can extract one type of features. A result obtained by applying a filter to the input image is referred to as a feature map, and the number of the feature maps is equal to the number of filters. A feature map output by a convolution layer of a level can be input into a convolution layer of a next adjacent level and is reprocessed to obtain a new feature map. For example, as shown in FIG. 2, a convolution layer of the first level may output a first feature map, the first feature map may be input into a convolution layer of the second level, and the convolution layer of the second level may process the first feature map to obtain a second feature map.

For example, a pooling layer is disposed between two adjacent convolution layers. On one hand, the pooling layer can be used to reduce a size of the input image or the feature maps, simplify computational complexity and reduce an over-fitting phenomenon to a certain degree; on the other hand, the pooling layer may also perform feature compression, so as to extract main features of the input image. For example, an input image with a size of 12×12 is sub-sampled by a filter with a size of 6×6, and then an output image with a size of 2×2 can be obtained. This means that 36 pixels on the input image are merged into one pixel in the output image. There are many methods to implement sub-sampling, and these methods comprise, but not limited to, maximal value pooling (max-pooling), average value pooling (avg-pooling), random pooling, decimation (such as selecting fixed pixels), demultiplexing output (demuxout, such as dividing the input image into a plurality of smaller images) and the like. Usually, a last pooling layer or a last convolution layer is connected to one or more fully-connected layers, which are used to connect all features of the input image. The output of the fully-connected layer is a one-dimensional matrix, that is, a vector. For example, according to actual needs, the fully-connected layer may be connected with a classifier, and the classifier may classify the input image based on the extracted features. A classification result of the classifier is output through an output layer as a final output of the convolutional neural network.

For example, in a case that the classifier is a Softmax classifier, each category label is given a certain prediction probability, and a category label having the largest prediction probability is selected as a label or a category of the input image.

For example, in a case that the classifier is an SVM classifier, each category label is given a certain classification score by its distance from a separating hyperplane, and a category label having the highest classification score is selected as a label or a category of the input image.

For example, in the step S201, the convolution layer in the convolutional neural network is used to extract features of a medical image. According to actual needs, each convolution layer may be provided with a plurality of filters, so as to extract various features of the medical image. The features of the medical image, for example, may comprise texture features, shape features, edge features and so on.

For example, in an embodiment of the present disclosure, the convolutional neural network may adopt models such as Inception-ResNet or GoogLeNet v3. Alternatively, the convolutional neural network may also use a convolutional neural network that is customized according to a medical image classification principle. The embodiments of the present disclosure are not limited thereto.

For example, in the step S202, the fully-connected layer inputs all the features of the medical image extracted by the convolution layer into the classifier. The classifier can classify the medical image based on all the features of the medical image to obtain the classification result.

For example, the step S202 may comprise the following steps:

Step 2021: based on the features of the medical image, calculating a plurality of scores if the medical image is classified to a plurality of different categories by the classifier;

Step 2022: determining the classification result of the medical image according to sorting of the plurality of scores.

For example, the classifier may comprise a Support Vector Machine (SVM) classifier, a Softmax classifier, a K-nearest neighbor (KNN) classifier and the like. For example, the Softmax classifier is a classifier that classifies the medical image based on the prediction probability, and the SVM classifier is a classifier that classifies the medical image based on the separating hyperplane.

For example, in a case that the classifier is the Softmax classifier, the Softmax classifier comprises a plurality of category labels, the plurality of scores is a plurality of prediction probabilities, and the plurality of prediction probabilities correspond to the plurality of category labels. The absolute values of the plurality of prediction probabilities indicate probabilities that the medical image belongs to different categories. The classification result corresponds to a maximum prediction probability among the plurality of prediction probabilities. For example, a category corresponding to the maximum prediction probability is the classification result output in the step S20.

For example, the classification result indicates a category of the medical image, and medical images of different categories have different types of features. For example, the classification result may be a fundus image, a brain tissue MRI image, a spinal cord MRI image, a blood vessel image, a pancreas CT image, a lung CT image and so on.

For example, in the step S30, the computer aided diagnosis device is configured to analyze features of the medical image corresponding to the classification result. The computer aided diagnosis device is a part of a computer aided diagnosis device group. The computer aided diagnosis device group comprises a plurality of computer aided diagnosis devices, and the plurality of computer aided diagnosis devices is configured to analyze features of medical images of different categories respectively. According to the classification result, the neural network may input the medical image into the computer aided diagnosis device corresponding to the classification result, and then the computer aided diagnosis device analyzes the medical image automatically. Therefore, the medical image analysis method provided by the embodiments of the present disclosure may achieve integration of a plurality of computer aided diagnosis devices.

For example, a quantity of the plurality of computer aided diagnosis devices in the computer aided diagnosis device group is identical as a quantity of the plurality of scores. The plurality of computer aided diagnosis devices is in one-to-one correspondence to the plurality of scores, so as to determine that a category corresponding to an computer aided diagnosis device with the highest score is the classification result of the medical image and to input the medical image into the computer aided diagnosis device for analysis. However, the present disclosure is not limited thereto, and the plurality of scores may also correspond to one computer aided diagnosis device.

For example, each computer aided diagnosis device in the computer aided diagnosis device group may analyze a feature of the medical image for a corresponding tissue (such as brain tissue, lungs, etc.), and may also analyze various features of the medical image for the corresponding tissue. The embodiments of the present disclosure are not limited thereto.

For example, the computer aided diagnosis device may detect, segment and analyze the medical image based on a convolutional neural network. The plurality of computer aided diagnosis devices may process the medical image by convolutional neural networks with the same structure, but may also process the medical image by convolutional neural networks with different structures. The embodiments of the present disclosure are not limited thereto.

For example, in an example, the classifier in the neural network is a SoftMax classifier, and assume that the SoftMax classifier has a first category label, a second category label and a third category label. The first category label indicates a fundus image, the second category label indicates a brain tissue MRI image, and the third category label indicates a lung CT image. After the medical image is processed by the neural network, the SoftMax classifier may output a first score, a second score and a third score, and the first score, the second score and the third score respectively represent a prediction probability of the first category label, a prediction probability of the second category label and a prediction probability of the third category label. For example, if the first score is 0.9, the second score is 0.04 and the third score is 0.06, the SoftMax classifier outputs the first category label corresponding to the first score, that is, the classification result is the first category label which represents that the input medical image is a fundus image. Therefore, the medical image can be transmitted into a computer aided diagnosis device corresponding to the first category label, and the computer aided diagnosis device can analyze fundus features of the medical image.

For example, in another example, the classifier of the neural network is an SVM classifier, and assume that the SVM classifier also has a first category label, a second category label and a third category label. The first category label indicates a fundus image, the second category label indicates a blood vessel image, and the third category label indicates a lung image. After the medical image is processed by the neural network, the SVM classifier may output a first score, a second score and a third score. The first score, the second score and the third score respectively represent a classification score of a distance of the first category label relative to a separating hyperplane, a classification score of a distance of the second category label relative to the separating hyperplane and a classification score of a distance of the third category label relative to the separating hyperplane. For example, if the first score is −2.6, the second score is 0.8 and the third score is 0.2, the SVM classifier outputs the second category label corresponding to the second score, that is, the classification result is the second category label which represents that the input medical image is a blood vessel image. Therefore, the medical image can be transmitted into a computer aided diagnosis device corresponding to the second category label, and the computer aided diagnosis device can analyze blood vessel features of the medical image.

For example, before performing the step S10, the medical image analysis method further comprises training the neural network by using different types of medical images. A training phase comprises training the neural network with sample images in a medical image database to generate parameters of the neural network.

For example, in the training phase, initial parameters of the neural network may be set as random numbers, and may also adopt parameters of a neural network which has been trained based on ImageNet and other image databases.

For example, the medical image database may comprise different types of sample images, so that parameters and feature models of the neural network corresponding to different types of medical images may be obtained. According to actual needs, the sample images may comprise different types of medical images, such as brain tissue MRI images, spinal cord MRI images, fundus images, blood vessel images, pancreas CT images, and lung CT images. For example, the sample images may comprise healthy medical images and diseased medical images. The sample images may comprise medical images obtained by sampling peoples from different age groups and different places, so as to improve classification accuracy and comprehensiveness of the neural network.

For example, when features of medical images of four different tissues need to be analyzed automatically, and the four tissues are fundus, lung nodule, brain tissue, and pancreas respectively, then the medical image database may comprise a fundus sample image group, a lung nodule sample image group, a brain tissue sample image group and a pancreas sample image group. For example, the fundus sample image group may comprise healthy fundus images and diseased fundus images. The remaining sample image groups are similar to the fundus sample image group.

For example, the training phase may comprise a back propagation process. In the back propagation process, a loss function may be used to calculate errors of the parameters of the neural network; and then, correction values for parameters of the neural network are calculated according to the errors, and the parameters of the neural network are corrected according to the correction values to obtain a better neural network model, so as to improve the classification accuracy of the medical images.

For example, the parameters of the neural network may comprise weights and biases of convolution layers.

For example, the loss function may comprise a log-likelihood loss function, a cross-entropy loss function, a Hinge loss function, an exponential loss function, a 0-1 loss function and so on.

For example, in a case that the classifier of the neural network is a SoftMax classifier, the loss function may be the log-likelihood loss function. In a case that the classifier of the neural network is an SVM classifier, the loss function may be the Hinge loss function.

For example, the log-likelihood loss function C is expressed as:

$$C = -\ln a_y$$

here, y denotes a category of the input medical image, and $a_y$ denotes a prediction probability corresponding to y. If the prediction probability of the y category is larger, the prediction probability $a_y$ gets closer to 1 and the log-likelihood loss function C gets closer to 0; if the prediction probability of the y category is smaller, the prediction probability $a_y$ gets closer to 0 and the log-likelihood loss function C gets closer to infinity. For example, the larger the log-likelihood loss function C is, the larger the correction values of the parameters of the neural network are.

For example, in an example, the SoftMax classifier has a first category label and a second category label. The first category label represents a fundus image and the second category label represents a brain tissue MRI image. An input sample image is a fundus image, so that a target classification result is the first category label. For example, after the neural network processes the sample image, the SoftMax classifier may output a first prediction probability and a second prediction probability. The first prediction probability is 0.4, and the second prediction probability is 0.6. Because the second prediction probability is larger than the first prediction probability, the SoftMax classifier outputs the second category label, that is, an actual classification result is the second category label which indicates that the input sample image is the brain tissue MRI image. The actual classification result is different from the target classification result, and therefore, the parameters of the neural network need to be corrected. For example, correcting the parameters of the neural network may comprise the following steps: firstly, the log-likelihood loss function C is calculated, and in the above case, y represents the fundus image, $a_y$ is the first prediction probability, that is, $a_y=0.4$, and $C=-\ln a_y=-\ln 0.4=0.9$; then, correction values of the parameters of the neural network may be calculated based on the log-likelihood loss function C; next, the parameters of the neural network are corrected according to the correction values. After the parameters of the neural network are corrected, the neural network processes the input sample image again, and the SoftMax classifier outputs a corrected first prediction probability and a corrected second prediction probability. For example, the corrected first prediction probability is 0.8 and the corrected second prediction probability is 0.2. Because the corrected first prediction probability is larger than the corrected second prediction probability, the SoftMax classifier outputs the first category label, that is, the actual classification result is the first category label which indicates that the input sample image is the fundus image. The actual classification result is the same as the target classification result. The above process is iterated to complete the training of the neural network.

It should be noted that, the above example only schematically illustrates the training process of the neural network. A person having ordinary skill in the art should know that in the training phase, the neural network needs to be trained by using a large number of sample images; meanwhile, in a training process of each sample image, the parameters of the neural network can be corrected through multiple repeated iterations.

It is worth noting that the training phase may comprises fine-tuning the parameters of the neural network to obtain more optimized parameters.

Figure 3:
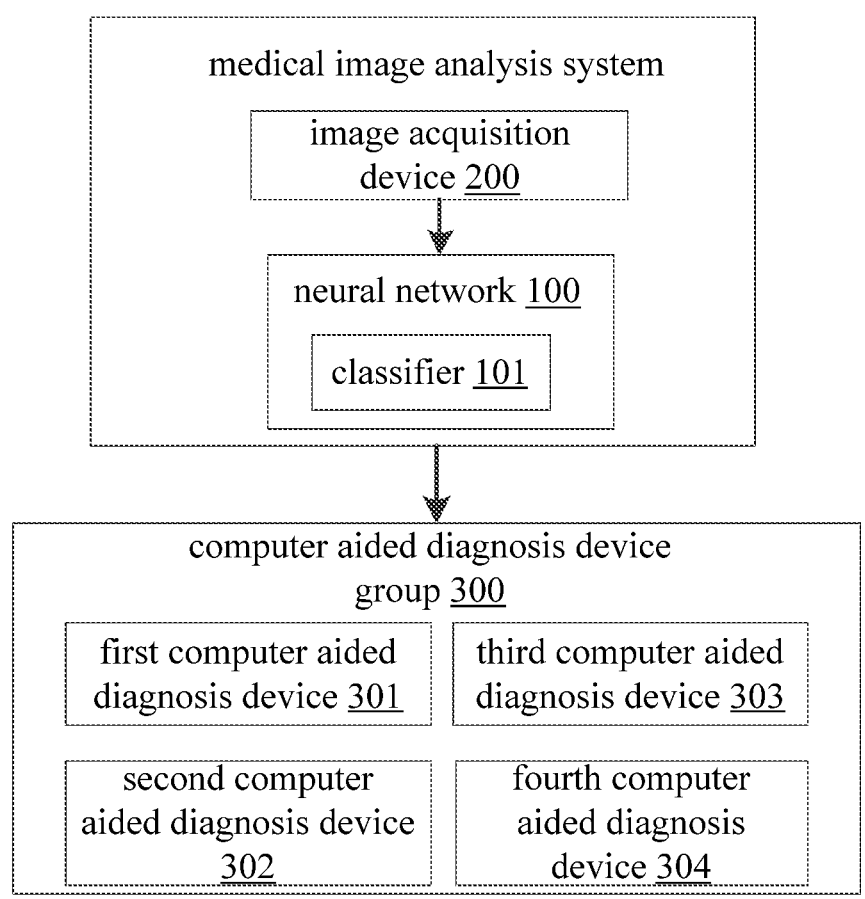
FIG. 3 is a schematic block diagram of a medical image analysis system provided by an embodiment of the present disclosure.
Figure 4:
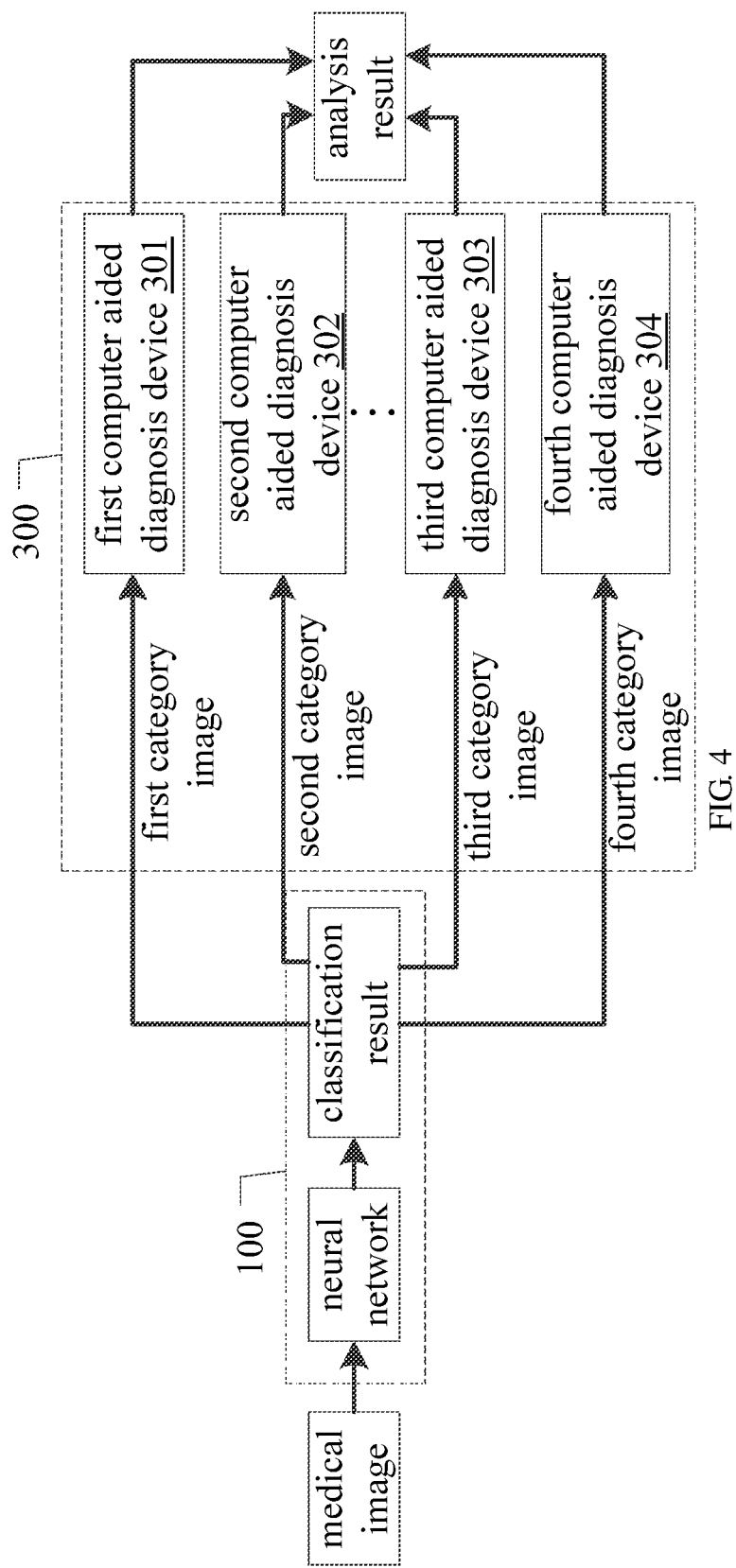
FIG. 4 is another schematic block diagram of a medical image analysis system provided by an embodiment of the present disclosure.

FIG. 3 is a schematic block diagram of a medical image analysis system provided by an embodiment of the present disclosure; FIG. 4 is another schematic block diagram of a medical image analysis system provided by an embodiment of the present disclosure.

For example, as shown in FIG. 3, a medical image analysis system provided by an embodiment of the present disclosure comprises a neural network 100 and an image acquisition device 200. The medical image analysis system is connected with a computer aided diagnosis device group 300. The image acquisition device 200 is connected with an input layer of the neural network 100, and the computer aided diagnosis device group 300 is connected with an output layer of the neural network 100.

The medical image analysis system provided by an embodiment of the present disclosure can integrate various types of medical-image computer aided diagnosis devices, so as to form a fully automatic medical image analysis system. The medical image analysis system can achieve automatically analyzing various kinds of medical images and alleviate scarcity and unevenness of medical resources.

For example, the image acquisition device 200 is configured to obtain a medical image.

For example, the neural network 100 is configured to receive and process the medical image, so as to determine a classification result of the medical image. The neural network 100 is also configured to input the medical image into a corresponding computer aided diagnosis device (for example, a first computer aided diagnosis device 301, a second computer aided diagnosis device 302, a third computer aided diagnosis device 303 or a fourth computer aided diagnosis device 304) in the computer aided diagnosis device group 300 according to the classification result. The corresponding computer aided diagnosis device is configured to analyze the medical image to obtain information of the medical image.

For example, the neural network 100 may be a convolutional neural network, so that a category of the medical image can be accurately determined and the classification accuracy of the medical image can be improved. The convolutional neural network may be a deep convolutional neural network. The neural network 100 can also be other types of deep convolutional neural networks.

For example, the convolutional neural network may adopt models such as Inception-ResNet or GoogLeNet v3. Alternatively, the convolutional neural network may also use a convolutional neural network that is customized according to a medical image classification principle.

For example, the neural network 100 may comprise an input layer, a convolution layer, a pooling layer, a fully-connected layer, a classifier 101, an output layer, etc. The convolution layer of the neural network 100 is configured to extract features of the medical image, and the classifier 101 is configured to classify the medical image based on the extracted features of the medical image to obtain a classification result. For example, when an operation of classifying the medical image based on the extracted features of the medical image is performed to obtain the classification result, the classifier 101 is configured to calculate a plurality of scores if the medical image is classified to a plurality of different categories based on the extracted features of the medical image, and determine the classification result of the medical image according to the sorting of the plurality of scores.

For example, the classifier 101 may comprise a SVM classifier, a Softmax classifier, a K-nearest neighbor (KNN) classifier and the like.

For example, in a case that the classifier 101 is the Softmax classifier, the plurality of scores is a plurality of prediction probabilities, and the classification result corresponds to a maximum prediction probability among the plurality of prediction probabilities.

For example, the computer aided diagnosis device group 300 comprises a plurality of computer aided diagnosis devices, and the plurality of computer aided diagnosis devices is configured to analyze features of medical images from different categories. As shown in FIG. 3, the plurality of computer aided diagnosis devices may comprise the first computer aided diagnosis device 301, the second computer aided diagnosis device 302, the third computer aided diagnosis device 303 and the fourth computer aided diagnosis device 304. It should be noted that the present disclosure includes, but not limited to, the example shown in FIG. 3.

For example, as shown in FIG. 4, each computer aided diagnosis device in the computer aided diagnosis device group 300 corresponds to a classification result, and is configured to analyze features of the medical image corresponding to the classification result. Each computer aided diagnosis device is further configured to output an analysis result for subsequent operations. For example, the classification result may comprise a first category image, a second category image, a third category image and a fourth category image; and the first category image is a fundus image, the second category image is a lung CT image, the third category image is a brain tissue MRI image, and the fourth category image is a pancreas CT image. In this case, the first computer aided diagnosis device 301 may be configured to analyze features of a medical image of a fundus tissue, the second computer aided diagnosis device 302 may be configured to analyze features of a medical image of a lung tissue, the third computer aided diagnosis device 303 may be configured to analyze features of a medical image of a brain tissue, and the fourth computer aided diagnosis device 304 may be configured to analyze features of a medical image of a pancreas tissue.

For example, each computer aided diagnosis device in the computer aided diagnosis device group 300 may analyze various types of features of a medical image of a corresponding tissue, and may also analyze a type of features of the medical image of the corresponding tissue. The second computer aided diagnosis device 302, for example, may be used to only analyze features of a lung nodule image of the lung tissue; alternatively, the second computer aided diagnosis device 302 may also be used to analyze features of various lung images, such as a lung nodule image, a tuberculosis image and an emphysema image, of the lung tissue.

For example, the number of the computer aided diagnosis device in the computer aided diagnosis device group 300 may be the same as or different from the number of the plurality of scores.

For example, in a case that multiple computer aided diagnosis devices in the computer aided diagnosis device group 300 are configured to analyze features of a medical image of a same tissue, the multiple computer aided diagnosis devices may correspond to one classification result. Therefore, the number of the plurality of computer aided diagnosis devices in the computer aided diagnosis device group 300 is more than the number of the plurality of scores. For example, the first computer aided diagnosis device 301 may be configured to analyze features of an emphysema image of the lung tissue, and the second computer aided diagnosis device 302 may be configured to analyze features of a lung nodule image of the lung tissue, so that when the classification result is a lung CT image, the medical image may be simultaneously input into the first computer aided diagnosis device 301 and the second computer aided diagnosis device 302.

It should be noted that, relevant detailed descriptions of the image acquisition device 200, the neural network 100, the computer aided diagnosis device group 300, the medical image, the prediction probability, the classification result and the like can be referred to in related descriptions in the embodiments of the medical image analysis method, and similar descriptions will be omitted here.

Figure 5:
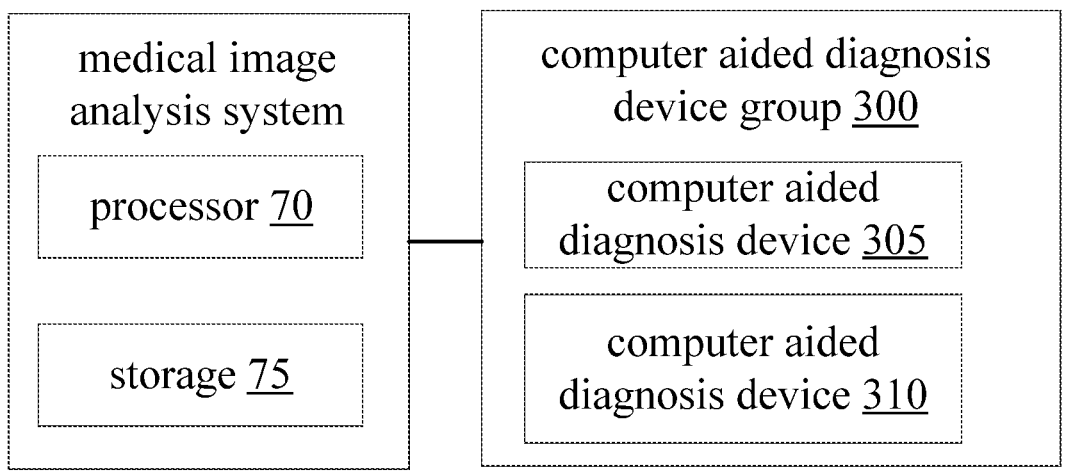
FIG. 5 is a schematic block diagram of a medical image analysis system provided by another embodiment of the present disclosure.

FIG. 5 is a schematic block diagram of a medical image analysis system provided by another embodiment of the present disclosure.

For example, as shown in FIG. 5, a medical image analysis system provided by an embodiment of the present disclosure comprises a processor 70 and a storage 75. The medical image analysis system is connected with a computer aided diagnosis device group 300. It should be noted that, components of the medical image analysis system shown in FIG. 5 are merely exemplary, but not limitative, and the medical image analysis system may further comprise other components according to actual application needs.

For example, the computer aided diagnosis device group 300 may comprise a plurality of computer aided diagnosis devices (for example, an computer aided diagnosis device 305 and an computer aided diagnosis device 310 shown in FIG. 5).

For example, the processor 70, the storage 75, each computer aided diagnosis device in the computer aided diagnosis device group 300 and other components may be connected and communicated with each other through a network.

For example, the network may comprise a wireless network, a wired network, and/or any combination of the wireless network and the wired network. The network may comprise a local area network, the Internet, a telecommunication network, Internet of things based on the Internet and/or the telecommunication network, and/or any combination of the above networks, and the like. For example, the wired network may communicate by means such as a twisted pair, coaxial cable or optical fiber transmission. The wireless network may communicate by means such as 3G/4G/5G mobile communication networks, Bluetooth, Zigbee or WiFi. The present disclosure does not limit types and functions of the network herein.

For example, the processor 70, the storage 75, each computer aided diagnosis device in the computer aided diagnosis device group 300 and other components may directly or indirectly communicate with each other.

For example, the processor 70 may control other components in the medical image analysis system to perform desired functions. The processor 70 may be a device having data processing capabilities and/or program execution capabilities, such as a central processing unit (CPU), or graphics processing unit (GPU), or a field programmable logic array (FPGA). The central processing unit (CPU) may be an X86, ARM architecture, or the like. The GPU may be integrated directly into a motherboard alone, or may be disposed into a north bridge chipset of the motherboard. The GPU may also be disposed on the central processing unit (CPU). Due to powerful image processing capabilities of the GPU, an embodiment of the present disclosure may use the GPU to train a convolutional neural network, and process an image based on the convolutional neural network.

For example, the storage 75 may comprise an arbitrary combination of one or more computer program products. The computer program products may comprise various forms of computer-readable storage media, such as volatile memory and/or non-volatile memory. The volatile memory may comprise, for example, a random access memory (RAM) and/or a cache or the like. The non-volatile memory may comprise, for example, a read only memory (ROM), a hard disk, an erasable programmable read only memory (EPROM), a portable compact disc-read only memory (CD-ROM), a USB memory, a flash memory, and the like. One or more computer instructions may be stored on the storage 75, and the processor 70 may execute the computer instructions to implement various functions. Various application programs and various data, such as sample images, training data, and various data used and/or generated by the application programs, and the like, may also be stored in the computer-readable storage medium.

For example, the medical image analysis system may further comprise an output device (not shown in FIG. 5). The output device may be used to output analysis results of the computer aided diagnosis device group 300. For example, the output device may be a monitor, a projector, and the like, so as to display the analysis results and/or medical images. A doctor can view the analysis results and/or the medical images through the monitor, a projection screen, or the like, and combine the analysis results and the medical images to perform disease diagnosis, treatment and other operations on a patient.

For example, the medical image analysis system may further comprise an input device (not shown in FIG. 5). The input device may be, for example, a keyboard, a mouse, a remote controller, a touch screen with a touch function, or the like. The input device may be used to receive instructions from an external computer device, from a user (such as a doctor), or the like. The doctor may use the input device to achieve interaction with the medical image analysis system.

For example, the computer instructions, as executed by the processor 70, cause the processor 70 to perform steps including: obtaining a medical image; processing the medical image by using a neural network, so as to determine a classification result of the medical image; and inputting the medical image into a computer aided diagnosis device corresponding to the classification result for analysis.

For example, in an example, the computer instructions, as executed by the processor 70, cause the processor 70 to perform a step of "processing the medical image by using the neural network, so as to determine the classification result of the medical image" including: extracting features of the medical image by the neural network; and classifying the medical image by a classifier based on features of the medical image to obtain the classification result.

For example, in an example, the computer instructions, as executed by the processor 70, cause the processor 70 to perform a step of "classifying the medical image by a classifier based on features of the medical image to obtain the classification result" including: based on the features of the medical image, calculating a plurality of scores that the medical image belongs to a plurality of different categories by the classifier; and determining the classification result of the medical image according to sorting of the plurality of scores.

For example, the classifier of the neural network may comprise a support vector machine (SVM) classifier, a SoftMax classifier and so on. In a case that the classifier is the Softmax classifier, the plurality of scores is a plurality of prediction probabilities, and the classification result corresponds to a maximum prediction probability among the plurality of prediction probabilities.

For example, the computer aided diagnosis device is configured to analyze features of a medical image corresponding to the classification result, the computer aided diagnosis device is a part of an computer aided diagnosis device group, and respective computer aided diagnosis devices in the computer aided diagnosis device group are configured to analyze features of medical images of different categories. The number of computer aided diagnosis device in the computer aided diagnosis device group may be the same as the number of the plurality of scores.

For example, in an example, the computer instructions, as executed by the processor 70, may further cause the processor 70 to perform the following steps including: in a training phase, training the neural network with sample images in a medical image database to generate parameters of the neural network.

For example, a loss function in the training phase may comprise a log-likelihood loss function, a cross-entropy loss function, a Hinge loss function, an exponential loss function, a 0-1 loss function and so on.

For example, the loss function in the training phase may be the log-likelihood loss function, and the log-likelihood loss function C is expressed as:

$$C = -\ln a_y$$

here, y denotes a category of the input medical image, and $a_y$ denotes a prediction probability corresponding to y. If the prediction probability of the y category is larger, the prediction probability $a_y$ gets closer to 1 and the log-likelihood loss function C gets closer to 0; if the prediction probability of the y category is smaller, the prediction probability $a_y$ gets closer to 0 and the log-likelihood loss function C gets closer to infinity. For example, the larger the log-likelihood loss function C is, the larger the correction values of parameters of the neural network are.

It should be noted that, relevant detailed descriptions of the neural network, the computer aided diagnosis device group, the loss function, the prediction probability, the classification result and the like can be referred to in related descriptions in the embodiments of the medical image analysis method, and similar descriptions will be omitted here.

At least one embodiment of the present disclosure further provides a storage medium. The storage medium stores non-transitory computer-readable instructions. The non-transitory computer-readable instructions, as executed by a computer, may perform one or more steps in the above-described medical image analysis method.

For example, in an example of the embodiments of the present disclosure, the storage medium may be applied in the medical image analysis system described in any one of the above embodiments. For example, the storage medium may be the storage 75 of the medical image analysis system.

For example, the description of the storage medium may be referred to in the description of the storage 75 in the embodiments of the medical image analysis system. Similar descriptions will be omitted here.

For the present disclosure, the following statements should be noted:

(1) the accompanying drawings involve only the structure(s) in connection with the embodiment(s) of the present disclosure, and other structure(s) can be referred to in common design(s); and (2) in case of no conflict, the embodiments of the present disclosure and the features in the embodiment(s) can be combined with each other to obtain new embodiment(s).

What have been described above are only specific implementations of the present disclosure, the protection scope of the present disclosure is not limited thereto, and the protection scope of the present disclosure should be based on the protection scope of the claims.

What is claimed is:

1. A medical image analysis method, comprising:
obtaining a medical image;
processing the medical image by using a neural network, so as to determine a classification result of the medical image; and
inputting the medical image into a plurality of computer aided diagnosis devices corresponding to the classification result,
wherein the plurality of computer aided diagnosis devices are configured to respectively analyze a plurality of different features of the medical image.

2. The medical image analysis method according to claim 1, wherein the processing the medical image by using the neural network, so as to determine the classification result of the medical image comprises:
extracting features of the medical image by the neural network; and
classifying the medical image by a classifier based on the features of the medical image to obtain the classification result.

3. The medical image analysis method according to claim 2, wherein the classifying the medical image by the classifier based on the features of the medical image to obtain the classification result comprises:
based on the features of the medical image, calculating a plurality of scores that the medical image belongs to a plurality of different categories by the classifier; and
determining the classification result of the medical image according to sorting of the plurality of scores.

4. The medical image analysis method according to claim 3, wherein the plurality of scores is a plurality of prediction probabilities, and the classification result corresponds to a maximum prediction probability from the plurality of prediction probabilities.

5. The medical image analysis method according to claim 3, wherein an computer aided diagnosis device group comprises the plurality of computer aided diagnosis devices, and part computer aided diagnosis devices of respective computer aided diagnosis devices in the computer aided diagnosis device group are configured to analyze features of medical images of different categories.

6. The medical image analysis method according to claim 5, wherein a quantity of computer aided diagnosis devices in the computer aided diagnosis device group is greater than a quantity of the plurality of scores.

7. The medical image analysis method according to claim 1, wherein before obtaining the medical image, the medical image analysis method further comprises:
in a training phase, training the neural network with sample images in a medical image database to generate a parameter of the neural network.

8. The medical image analysis method according to claim 7, wherein a loss function in the training phase comprises a log-likelihood loss function, and the log-likelihood loss function is expressed as:

$$C = -\ln a_y$$

wherein C denotes the log-likelihood loss function, y denotes a category of the medical image, and $a_y$ denotes a prediction probability corresponding to y.

9. A medical image analysis system, connected with a plurality of computer aided diagnosis devices, comprising:
a neural network, comprising an input layer and an output layer;
an image acquisition device connected with the input layer of the neural network; and
the plurality of computer aided diagnosis devices being connected with the output layer of the neural network, wherein:
the image acquisition device is configured to obtain a medical image;
the neural network is configured to:
receive and process the medical image, so as to determine a classification result of the medical image, and
input the medical image into the plurality of computer aided diagnosis devices according to the classification result; and
the plurality of computer aided diagnosis devices are configured to respectively analyze a plurality of different features of the medical image.

10. The medical image analysis system according to claim 9, wherein the neural network comprises a classifier, the neural network is configured to extract features of the medical image, and the classifier is configured to classify the medical image based on the features of the medical image to obtain the classification result.

11. The medical image analysis system according to claim 10, wherein the classifier comprises at least one of a support vector machine (SVM) classifier and a SoftMax classifier.

12. The medical image analysis system according to claim 11, wherein the classifier is configured to:
based on the features of the medical image, calculate a plurality of scores that the medical image belongs to a plurality of different categories; and
determine the classification result of the medical image according to sorting of the plurality of scores.

13. The medical image analysis system according to claim 12, wherein the plurality of scores is a plurality of prediction probabilities, and the classification result corresponds to a maximum prediction probability from the plurality of prediction probabilities.

14. The medical image analysis system according to claim 13, wherein an computer aided diagnosis device group comprises the plurality of computer aided diagnosis devices, and part computer aided diagnosis devices of respective computer aided diagnosis devices of the computer aided diagnosis device group are configured to analyze features of medical images of different categories.

15. The medical image analysis system according to claim 14, wherein a quantity of computer aided diagnosis devices in the computer aided diagnosis device group is greater than a quantity of the plurality of scores.

16. The medical image analysis system according to claim 9, wherein the neural network is a convolutional neural network.

17. A medical image analysis system, connected with a plurality of computer aided diagnosis devices, comprising:
a storage, configured to store non-transitory computer-readable instructions; and
a processor, configured to execute the non-transitory computer-readable instructions, wherein the non-transitory computer-readable instructions, as executed by the processor, cause the processor to perform steps including:
obtaining a medical image;
processing the medical image by using a neural network, so as to determine a classification result of the medical image; and
inputting the medical image into the plurality of computer aided diagnosis devices corresponding to the classification result,
wherein the plurality of computer aided diagnosis devices are configured to respectively analyze a plurality of different features of the medical image.

18. The medical image analysis system according to claim 17, wherein processing the medical image by using the neural network, so as to determine the classification result of the medical image comprises:
extracting features of the medical image by the neural network; and
classifying the medical image by a classifier based on the features of the medical image to obtain the classification result.

19. The medical image analysis system according to claim 18, wherein classifying the medical image by the classifier based on the features of the medical image to obtain the classification result comprises:
based on the features of the medical image, calculating a plurality of scores that the medical image belongs to a plurality of different categories by the classifier; and
determining the classification result of the medical image according to sorting of the plurality of scores.

20. A storage medium, configured to store non-transitory computer-readable instructions, wherein the non-transitory computer-readable instructions, as executed by a computer, cause the computer to perform the medical image analysis method according to claim 1.

* * * * *